United States Patent
Wolf et al.

(10) Patent No.: US 9,062,012 B2
(45) Date of Patent: Jun. 23, 2015

(54) PROCESS FOR MANUFACTURING 4-SUBSTITUTED AMINO-BENZOXAZINONES

(71) Applicants: Bernd Wolf, Niederkirchen (DE); Joachim Gebhardt, Wachenheim (DE); Uwe Josef Vogelbacher, Ludwigshafen (DE); Maximilian Dochnahl, Mannheim (DE); Michael Rack, Eppelheim (DE); Michael Keil, Freinsheim (DE); Timo Frassetto, Mannheim (DE); Volker Maywald, Ludwigshafen (DE)

(72) Inventors: Bernd Wolf, Niederkirchen (DE); Joachim Gebhardt, Wachenheim (DE); Uwe Josef Vogelbacher, Ludwigshafen (DE); Maximilian Dochnahl, Mannheim (DE); Michael Rack, Eppelheim (DE); Michael Keil, Freinsheim (DE); Timo Frassetto, Mannheim (DE); Volker Maywald, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/365,774

(22) PCT Filed: Dec. 20, 2012

(86) PCT No.: PCT/EP2012/076378
§ 371 (c)(1),
(2) Date: Jun. 16, 2014

(87) PCT Pub. No.: WO2013/092859
PCT Pub. Date: Jun. 27, 2013

(65) Prior Publication Data
US 2015/0018545 A1    Jan. 15, 2015

(30) Foreign Application Priority Data
Dec. 23, 2011 (EP) ................... 11195518

(51) Int. Cl.
*C07D 265/36* (2006.01)
*C07D 413/04* (2006.01)

(52) U.S. Cl.
CPC ............ *C07D 265/36* (2013.01); *C07D 413/04* (2013.01)

(58) Field of Classification Search
USPC ......................................... 544/105
See application file for complete search history.

(56) References Cited

FOREIGN PATENT DOCUMENTS

| EP | 170 191 | 2/1986 |
| JP | 62-221677 | 9/1987 |
| WO | WO 2010/145992 | 12/2010 |

OTHER PUBLICATIONS

International Search Report dated Feb. 27, 2013, prepared in International Application No. PCT/EP2012/076378.
International Preliminary Report on Patentability dated Jun. 24, 2014, prepared in International Application No. PCT/EP2012/076378.
Johnson, D.A., "Nonenzymatic conversion of penicillins to 6-aminopenicullanic Acid", Journal of Organic Chemistry, Aug. 1, 1966, p. 2560-2564, vol. 31, No. 8.
Techer, Henri, et al. "Tertiary amides of 3-oxo-2,3-dihydro-1,4-benzoxazine-2-carboxylic acid", C.R. Acad. Sc. Paris, Jan. 5, 1970, p. pp. 107-110, vol. 270.

*Primary Examiner* — Kahsay Habte
(74) *Attorney, Agent, or Firm* — Brinks Gilson & Lione

(57) ABSTRACT

The present invention relates to a process for manufacturing 4-substituted amino-benzoxazinones of formula (I),

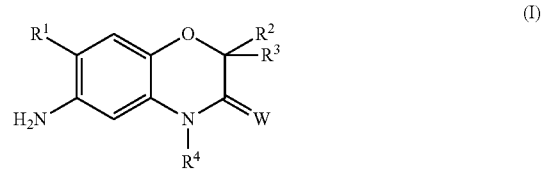

by reacting a NH-benzoxazinone of formula (II) with a compound of formula (III); wherein the variables are defined according to the description.

8 Claims, No Drawings

PROCESS FOR MANUFACTURING 4-SUBSTITUTED AMINO-BENZOXAZINONES

This application is a National Stage application, of International Application No. PCT/EP2012/076378, filed Dec. 20, 2012, the entire contents of which is hereby incorporated herein by reference. This application also claims priority under 35 U.S.C. §119 to European Patent Application No. 11195518.3 filed Dec. 23, 2011, the entire contents of which is hereby incorporated herein by reference.

The invention relates to 4-substituted amino-benzoxazinones of formula (I), a process for manufacturing the 4-substituted amino-benzoxazinones of formula (I), their use in and a process for manufacturing triazinon-benzoxazinones of formula (IV).

WO 2010/145992 discloses a process for the preparation of amino-benzoxazinones by first alkylation of the 4-position of nitro-benzoxazinones and then subsequent reduction of the nitro substituent.

EP 170 191 describes the alkylation of benzoxazinones, which are in 2-position of the benzoxazinone ring preferably unsubstituted or substituted by an alkyl group.

However, there is still room for improvement, specifically in view of economical and ecological aspects.

One task of the invention is to provide an improved process for manufacturing 4-substituted amino-benzoxazinones of formula (I). A further task of the invention is to provide an improved process for manufacturing triazinon-benzoxazinones of formula (IV).

Surprisingly, it has been found that benzoxazinones bearing at least one halogen atom in the 2-position and a free amino group in the 6-position can be substituted, particularly alkylated, in the 4-position of the benzoxazinone ring. The corresponding 4-substituted amino-benzoxazinones of formula (I) can be obtained in high yields and excellent regioselectivities.

Accordingly, in one aspect of the invention there is provided a process for manufacturing 4-substituted amino-benzoxazinones of formula (I),

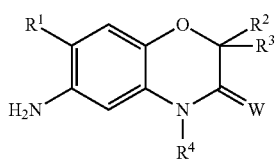

wherein
$R^1$ is H or halogen;
$R^2$ is halogen;
$R^3$ is H or halogen;
$R^4$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl; and
W is O or S;

by reacting a NH-benzoxazinone of formula (II),

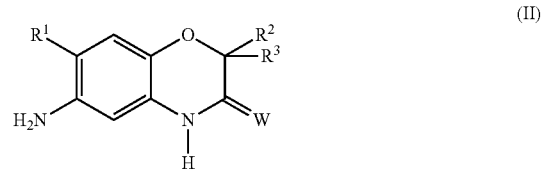

or a salt thereof,
wherein $R^1$, $R^2$, $R^3$ and W are defined as in formula (I);
with a compound of formula (III),

wherein $R^4$ is defined as in formula (I);
L is halogen or $OS(O)_2R^7$; and
$R^7$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl ring independently of one another is unsubstituted or substituted with 1 to 5 substituents selected from the group consisting of halogen, CN, $NO_2$, $C_1$-$C_6$-alkyl, $C_1$-$C_6$-haloalkyl or $C_1$-$C_6$-alkoxy;
optionally in the presence of a base.

In a further aspect of the invention there is provided a process for preparing triazinon-benzoxazinones of formula (IV),

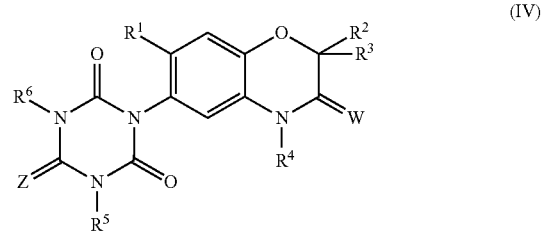

wherein $R^1$, $R^2$, $R^3$, $R^4$ and W are defined as in formula (I);
$R^5$ is H, $NH_2$, $C_1$-$C_6$-alkyl or $C_3$-$C_6$-alkynyl;
$R^6$ is H or $C_1$-$C_6$-alkyl; and
Z is O or S.

In a further aspect of the invention there is provided the use of 4-substituted amino-benzoxazinones of formula (I) in manufacturing triazinon-benzoxazinones of formula (IV). In a further aspect of the invention there is provided the use of NH-benzoxazinones of formula (II) in manufacturing triazinon-benzoxazinones of formula (IV).

The process of the invention gives 4-substituted amino-benzoxazinones of formula (I) in excellent yields, and thus, can be used in the synthesis of triazinon-benzoxazinones of formula (IV) in high yields and purities.

The process of the invention opens up the possibility to reduce the nitro group prior to introducing the substituent in the 4-position.

Hence, the present invention allows for more flexibility in the synthesis of benzoxazinones since it allows the introduction of substituents that are incompatible with reaction conditions under which an aromatic nitro group is converted into the corresponding amino group.

The NH-benzoxazinones of formula (II) as described herein can also be employed in the form of their salts. Suitable are, in general, those salts of the NH-benzoxazinone of formula (II), which cations have no adverse effect on the reaction.

Preferred cations are the ions of the alkali metals, preferably of lithium, sodium, potassium, rubidium and cesium, of the alkaline earth metals, preferably of magnesium, calcium and barium, of the transition metals, preferably of titanium, manganese, iron, copper, silver and zinc, and of the elements boron, aluminum and tin.

Especially preferred the NH-benzoxazinones of formula (II) as described herein are employed in form of their alkali metal or alkaline metal salts.

Particular preference is given to the cations of alkali metals, preferably lithium, sodium and potassium.

The organic moieties mentioned in the definition of the variables according to the present invention, e.g. $R^1$ to $R^7$ are—like the term halogen—collective terms for individual enumerations of the individual group members.

The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-cynaoalkyl, $C_1$-$C_6$-nitroalkyl, $C_1$-$C_6$-hydroxyalkyl, $C_1$-$C_6$-alkyoxy-$C_1$-$C_6$-alkyl, $C_3$-$C_6$-cycloalkyl-$C_1$-$C_4$-alkyl, amino-$C_1$-$C_6$-alkyl, ($C_1$-$C_6$-alkyl)amino-$C_1$-$C_6$-alkyl and di($C_1$-$C_6$-alkyl)amino-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl: $C_3$-$C_6$-alkenyl as mentioned above, and also ethenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl: $C_3$-$C_6$-alkynyl as mentioned above and also ethynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut- 2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

($C_1$-$C_4$-alkyl)amino: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino and also the ($C_1$-$C_6$-alkyl)amino moieties of ($C_1$-$C_6$-alkyl)amino-$C_1$-$C_6$-alkyl: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino and also the di($C_1$-$C_6$-alkyl)amino moieties of di($C_1$-$C_6$-alkyl)amino-$C_1$-$C_6$-alkyl: di($C_1$-$C_4$-alkyl)amino as mentioned above, and also, for example, N-methyl-N-pentylamino, N-methyl-N-(1-methylbutyl)amino, N-methyl-N-(2-methylbutyl) amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl) amino, N-ethyl-N-(3-methylpentyl)amino, N-ethyl-N-(4-methylpentyl)amino, N-ethyl-N-(1,1-dimethylbutyl) amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl) amino, N-ethyl-N-(3,3-dimethylbutyl)amino, N-ethyl-N-(1-ethylbutyl)amino, N-ethyl-N-(2-ethylbutyl) amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

saturated or aromatic 3- to 6-membered ring optionally containing 1 to 3 additional heteroatoms selected from the group O, S and N:

a monocyclic, saturated or aromatic cycle having three to six ring members which comprises apart from one nitrogen atom and carbon atoms optionally additionally one to three heteroatoms selected from the group O, S and N, for example: 1-aziridinyl, 1-azetidinyl; 1-pyrrolidinyl, 2-isothiazolidinyl, 2-isothiazolidinyl, 1-pyrazolidinyl, 3-oxazolidinyl, 3-thiazolidinyl, 1-imidazolidinyl, 1,2,4-triazolidin-1-yl, 1,2,4-oxadiazolidin-2-yl, 1,2,4-oxadiazolidin-4-yl, 1,2,4-thiadiazolidin-2-yl, 1,2,4-thiadiazolidin-4-yl; 1-pyrrolyl, 1-pyrazolyl, 1-imidazolyl, 1,2,3-triazol-1-yl, 1,2,4-triazol-1-yl, 1-tetrazolyl; 1-piperidinyl, 1-hexahydropyridazinyl, 1-hexahydropyrimidinyl, 1-piperazinyl, 1,3,5-hexahydrotriazin-1-yl, 1,2,4-hexahydrotriazin-1-yl, tetrahydro-1,3-oxazin-1-yl, 1-morpholinyl.

The preferred embodiments of the invention mentioned herein below have to be understood as being preferred either independently from each other or in combination with one another.

According to a preferred embodiment of the invention preference is also given to the preparation of those 4-substituted amino-benzoxazinones of formula (I), wherein the variables, either independently of one another or in combination with one another, have the following meanings:

$R^1$ is preferably H or F; particularly preferred H;
is also preferably halogen, particularly preferred F or Cl, especially preferred F;

$R^2$ is preferably Cl or F, particularly preferred F;
$R^3$ is preferably H, Cl or F, particularly preferred H or F, especially preferred H;
   is also preferably halogen, particularly preferred F or Cl, especially preferred F;
$R^4$ is preferably $C_3$-$C_6$-alkynyl or $C_3$-$C_6$-haloalkynyl, more preferably $C_3$-alkynyl or $C_3$-haloalkynyl, particularly preferred $CH_2C{\equiv}CH$, $CH_2C{\equiv}CCl$ or $CH_2C{\equiv}CBr$;
   is also preferably $C_3$-$C_6$-alkynyl or $C_3$-$C_6$-cycloalkyl-$C_1$-$C_6$-alkyl, particularly preferred propargyl or cyclopropylmethyl;
   is also preferably $C_3$-$C_6$-alkynyl, more preferably $C_3$-alkynyl; particularly preferred $CH_2C{\equiv}CH$;
   is also preferably $C_3$-$C_6$-haloalkynyl, more preferably $C_3$-haloalkynyl, particularly preferred $CH_2C{\equiv}CCl$ or $CH_2C{\equiv}CBr$;
W is preferably O,
   is also preferably S.

Particular preference is also given to the preparation of 4-substituted amino-benzoxazinones of formula (I.a), which correspond to 4-substituted amino-benzoxazinones of formula (I) wherein $R^2$ is F and W is O:

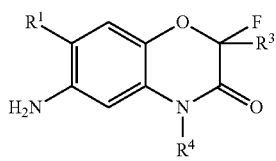

(I.a)

wherein the variables $R^1$, $R^3$ and $R^4$ have the meanings, in particular the preferred meanings, as defined above;
most preference to the preparation of 4-substituted amino-benzoxazinones of formulae (I.a.1) to (I.a.54) of Table A listed below, in which the variables $R^1$, $R^3$ and $R^4$ together have the meanings given in one row of Table A (4-substituted amino-benzoxazinones of formulae I.a.1 to I.a.54); and where the definitions of the variables $R^1$, $R^3$ and $R^4$ are of particular importance for the process and the compounds according to the invention not only in combination with one another but in each case also on their own:

TABLE A

| No. | $R^1$ | $R^3$ | $R^4$ |
|---|---|---|---|
| I.a.1. | H | H | H |
| I.a.2. | H | H | $CH_3$ |
| I.a.3. | H | H | $C_2H_5$ |
| I.a.4. | H | H | $CH_2$—$C_2H_5$ |
| I.a.5. | H | H | $CH(CH_3)_2$ |
| I.a.6. | H | H | $CH_2$—$CH_2$—$(CH_3)_2$ |
| I.a.7. | H | H | $CH_2$—$CH{=}CH_2$ |
| I.a.8. | H | H | $CH_2C{\equiv}CH$ |
| I.a.9. | H | H | $CH_2C{\equiv}C$—Br |
| I.a.10. | H | F | H |
| I.a.11. | H | F | $CH_3$ |
| I.a.12. | H | F | $C_2H_5$ |
| I.a.13. | H | F | $CH_2$—$C_2H_5$ |
| I.a.14. | H | F | $CH(CH_3)_2$ |
| I.a.15. | H | F | $CH_2$—$CH_2$—$(CH_3)_2$ |
| I.a.16. | H | F | $CH_2$—$CH{=}CH_2$ |
| I.a.17. | H | F | $CH_2C{\equiv}CH$ |
| I.a.18. | H | F | $CH_2C{\equiv}C$—Br |
| I.a.19. | F | H | H |
| I.a.20. | F | H | $CH_3$ |
| I.a.21. | F | H | $C_2H_5$ |
| I.a.22. | F | H | $CH_2$—$C_2H_5$ |
| I.a.23. | F | H | $CH(CH_3)_2$ |

TABLE A-continued

| No. | $R^1$ | $R^3$ | $R^4$ |
|---|---|---|---|
| I.a.24. | F | H | $CH_2$—$CH_2$—$(CH_3)_2$ |
| I.a.25. | F | H | $CH_2$—$CH{=}CH_2$ |
| I.a.26. | F | H | $CH_2C{\equiv}CH$ |
| I.a.27. | F | H | $CH_2C{\equiv}C$—Br |
| I.a.28. | F | F | H |
| I.a.29. | F | F | $CH_3$ |
| I.a.30. | F | F | $C_2H_5$ |
| I.a.31. | F | F | $CH_2$—$C_2H_5$ |
| I.a.32. | F | F | $CH(CH_3)_2$ |
| I.a.33. | F | F | $CH_2$—$CH_2$—$(CH_3)_2$ |
| I.a.34. | F | F | $CH_2$—$CH{=}CH_2$ |
| I.a.35. | F | F | $CH_2C{\equiv}CH$ |
| I.a.36. | F | F | $CH_2C{\equiv}C$—Br |
| I.a.37. | Cl | H | H |
| I.a.38. | Cl | H | $CH_3$ |
| I.a.39. | Cl | H | $C_2H_5$ |
| I.a.40. | Cl | H | $CH_2$—$C_2H_5$ |
| I.a.41. | Cl | H | $CH(CH_3)_2$ |
| I.a.42. | Cl | H | $CH_2$—$CH_2$—$(CH_3)_2$ |
| I.a.43. | Cl | H | $CH_2$—$CH{=}CH_2$ |
| I.a.44. | Cl | H | $CH_2C{\equiv}CH$ |
| I.a.45. | Cl | H | $CH_2C{\equiv}C$—Br |
| I.a.46. | Cl | F | H |
| I.a.47. | Cl | F | $CH_3$ |
| I.a.48. | Cl | F | $C_2H_5$ |
| I.a.49. | Cl | F | $CH_2$—$C_2H_5$ |
| I.a.50. | Cl | F | $CH(CH_3)_2$ |
| I.a.51. | Cl | F | $CH_2$—$CH_2$—$(CH_3)_2$ |
| I.a.52. | Cl | F | $CH_2$—$CH{=}CH_2$ |
| I.a.53. | Cl | F | $CH_2C{\equiv}CH$ |
| I.a.54. | Cl | F | $CH_2C{\equiv}C$—Br |

Very particular preference is given to the preparation of the 4-substituted amino-benzoxazinone of formula (I.a.35) as defined above:

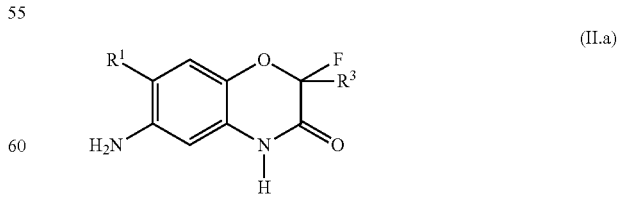

(I.a.35)

With respect to the variables within the NH-benzoxazinones of formula (II) necessary for the process according to the invention, the particularly preferred embodiments of the NH-benzoxazinones of formula (II) correspond, either independently of one another or in combination with one another, to those of the variables of $R^1$, $R^2$, $R^3$ and W of formula (I).

Particular preference is also given to the NH-benzoxazinones of formula (II.a) (corresponds to formula (II) wherein $R^2$ is F and W is O),

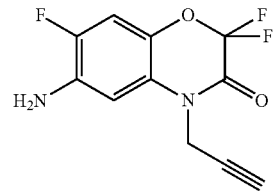

(II.a)

wherein the variables $R^1$ and $R^3$ have the meanings, in particular the preferred meanings, as defined above;
most preference to the amino-benzoxazinones of formulae (II.a.1) to (II.a.6) of Table B listed below, in which the variables R¹ and R³ together have the meanings given in one row of Table B (amino-benzoxazinones of formulae II.a.1 to II.a.6); and where the definitions of the variables R¹ and R³ are of particular importance for the process and the compounds according to the invention not only in combination with one another but in each case also on their own:

TABLE B

| No. | R¹ | R³ |
|---|---|---|
| II.a.1. | H | H |
| II.a.2. | H | F |
| II.a.3. | F | H |
| II.a.4. | F | F |
| II.a.5. | Cl | H |
| II.a.6. | Cl | F |

Very particular preference is given to the amino-benzoxazinone of formula (II.a.4) as defined above:

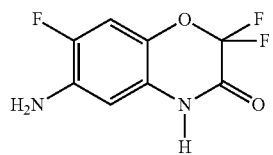

(II.a.4)

In one preferred embodiment of the invention the NH-benzoxazinone of formula (II) is employed.

In another preferred embodiment of the invention a salt of the NH-benzoxazinone of formula (II) is employed.

The NH-benzoxazinone of formula (II) necessary for the process according to the invention can be prepared as described further below.

With respect to the variables within the compounds of formula (III), the particularly preferred embodiments of the compounds of formula (III) correspond, either independently of one another or in combination with one another, to those of the variables of $R^4$ of formula (I), or have, either independently of one another or in combination with one another, the following meanings:

L is preferably halogen or $OS(O_2)R^7$,
  wherein $R^7$ is $C_1$-$C_6$-alkyl, phenyl or phenyl-$C_1$-$C_6$-alkyl, wherein each phenyl ring independently of one another is unsubstituted or substituted by 1 to 3 $C_1$-$C_6$-alkyl substituents;
  particularly preferred halogen or $OS(O_2)R^7$,
  wherein $R^7$ is $C_1$-$C_6$-alkyl or phenyl, wherein the phenyl ring is unsubstituted or substituted by 1 to 3 $C_1$-$C_6$-alkyl substituents;
  especially preferred Cl, Br, $OS(O)_2CH_3$ or $OS(O)_2(C_6H_4)CH_3$.

With respect to the compounds of formula (III), particular preference is given to propargyl chloride, propargyl bromide, propargyl mesylate or propargyl tosylate, which correspond to compounds of formula (III) wherein $R^4$ is propargyl and L is Cl, Br, $OS(O)_2CH_3$ or $OS(O)_2(C_6H_4)CH_3$.

The compounds of formula (III) are commercially available or can be prepared by methods known in the art Preferably the NH-benzoxazinone of formula (II) or a salt thereof is used in excess with regard to the compound of formula (III). Particularly preferred the molar ratio of the NH-benzoxazinone of formula (II) or a salt thereof to the compound of formula (III) is in the range from 1:1 to 1:2, especially preferred from 1:1 to 1:1.3, more preferably 1:1.

In one preferred embodiment of the invention a salt of the NH-benzoxazinone of formula (II) is employed, and the reaction of the salt of the NH-benzoxazinone of formula (II) with the compound of formula (III) is carried out in the absence of a base.

In another preferred embodiment of the invention the NH-benzoxazinone of formula (II) is employed, and the reaction of the NH-benzoxazinone of formula (II) with the compound of formula (III) is carried out in the presence of a base.

Examples of suitable bases are carbonates such as lithium carbonate, sodium carbonate, potassium carbonate, cesium carbonate, magnesium carbonate, calcium carbonate, barium carbonate; hydrogen carbonates such as lithium hydrogen carbonate, sodium hydrogen carbonate, potassium hydrogen carbonate; hydroxides such as lithium hydroxide, sodium hydroxide, potassium hydroxide, magnesium hydroxide, calcium hydroxide, barium hydroxide, aluminum hydroxide; oxides such as lithium oxide, sodium oxide, potassium oxide, magnesium oxide, calcium oxide, barium oxide, iron oxide, silver oxide; hydrides such as lithium hydride, sodium hydride, potassium hydride, calcium hydride; phosphates such as potassium phosphate, calcium phosphate; alkoxides such sodium, potassium or magnesium alkoxides.

Preferred bases are selected from the group consisting of carbonates, hydrogen carbonates, hydroxides, oxides, phosphates and alkoxides.

Preferred bases are selected from the group consisting of carbonates, hydroxides and alkoxides;
particularly preferred bases are carbonates.

The term base as used herein also includes mixtures of two or more, preferably two of the above compounds. Particular preference is given to the use of one base.

If a base is employed, preferably the base is used in excess with regard to the NH-benzoxazinone of formula (II).

Particularly preferred the number of base equivalents with regard to the NH-benzoxazinone of formula (II) is in the range from 1:0.5 to 1:3, especially preferred from 1:0.5 to 1:2, more preferably 1:0.5 to 1:1.3.

Preferably, the reaction of the compound of formula (III) with the NH-benzoxazinone of formula (II) and a base or with a salt of the NH-benzoxazinone of formula (II) is carried out in a solvent.

Examples of suitable solvents are dipolar aprotic solvents such as N,N-dimethylformamide (DMF), N,N-dimethylacetamide (DMAC), 1-methyl-2-pyrrolidinone (NMP), 1,3-dimethyl-2-imidazolidinone (DMI), N,N'-dimethylpropyleneurea (DMPU), dimethyl sulfoxide (DMSO), acetonitrile, acetone, methyl ethyl ketone, methyl butyl ketone, cyclohexanone, sulfolane, nitromethane; esters such as ethyl acetate; ethers such as dibutylether, tert-butyl methyl ether (TBME), tetrahydrofurane (THF), dioxane; alcohols such as methanol, ethanol, isoproponal, tert-butanol; halogenated hydrocarbons such as chloroform, dichloroethane, carbon tetrachloride; aliphatic hydrocarbons such as hexanes, cyclohexane; aromatic hydrocarbons such as benzene, toluene, cresols, chlorobenzene.

Preferred solvents include ethyl acetate, N,N-dimethylformamide (DMF) or N,N-dimethylacetamide (DMAC).

More preferred solvents include ethyl acetate or N,N-dimethylformamide (DMF).

The term solvent as used herein also includes mixtures of two or more of the above compounds.

The reaction of the compound of formula (III) with the NH-benzoxazinone of formula (II) and a base or with a salt of the NH-benzoxazinone of formula (II) is generally carried out at a temperature in the range from 0 to 150° C., preferably in the range from 20 to 100° C., more preferably in the range of from 50 to 85° C.

After completion or partial completion of the reaction, the respective mixture can be worked up by means of standard techniques. Examples thereof include filtration, aqueous work-up, evaporation of solvents and/or other volatile compounds. These methods can also be combined with each other.

In one preferred embodiment the reaction mixture is brought to room temperature and subjected to an aqueous work-up. The organic phase can be dried, e.g. by azeotropic distillation.

In one embodiment the crude product is purified, for example by crystallization, recrystallization or column chromatography.

In another embodiment the crude product is used without further purification.

The purity of the 4-substituted amino-benzoxazinone (I) is preferably at least 95%, more preferably at least 98%, determined by HPLC, if compound (I) is isolated and not used as a solution in the following step.

4-Substituted amino-benzoxazinones of formula (I) are useful in the synthesis of triazinon-benzoxazinones of formula (IV):

Triazinon-benzoxazinones of formula (IV) can be prepared by reacting 4-substituted amino-benzoxazinones of formula (I) with 1,1'-carbonyldiimidazole (CDI) and a (thio) urea compound of formula (V):

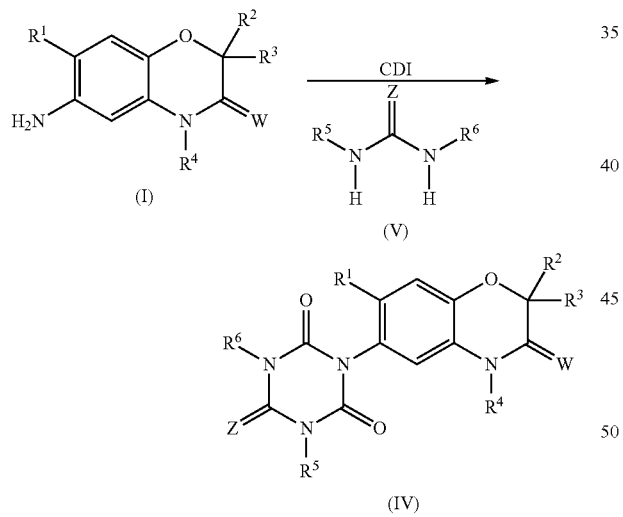

wherein
$R^1$, $R^2$, $R^3$, $R^4$, $R^5$, $R^6$, W and Z are defined as in formula (IV) above.

Preferably, the reaction of the 4-substituted amino-benzoxazinone of formula (I) with 1,1'-carbonyldiimidazole (CDI) and the (thio)urea compound of formula (V) to obtain the triazinon-benzoxazinone of formula (IV) is carried out in the presence of a base.

Accordingly, in a further preferred embodiment of the process of the invention triazinon-benzoxazinones of formula (IV) are obtained by i) reacting the NH-benzoxazinone of formula (II),

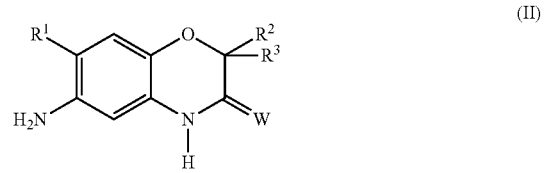

wherein $R^1$, $R^2$, $R^3$ and W are defined as above;
with a base and a compound of formula (III),

wherein $R^4$ and L are defined as above;
to obtain the 4-substituted amino-benzoxazinone of formula (I); and
ii) reacting the 4-substituted amino-benzoxazinone of formula (I) with 1,1'-carbonyldiimidazole (CDI) and a (thio) urea compound of formula (V) to obtain the triazinon-benzoxazinone of formula (IV).

In another embodiment of the process according to the invention, the 4-substituted amino-benzoxazinone of formula (I) is further converted into a triazinon-benzoxazinone of formula (IV),

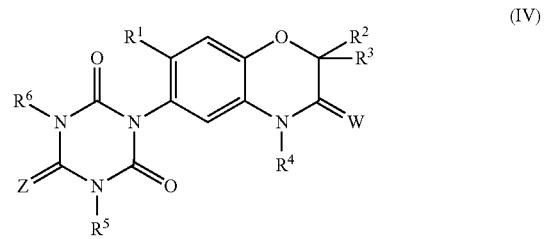

wherein
$R^1$ is H or halogen;
$R^2$ is halogen;
$R^3$ is H or halogen;
$R^4$ is $C_1$-$C_6$ alkyl, $C_1$-$C_6$ haloalkyl, $C_3$-$C_6$ cycloalkyl, $C_3$-$C_6$ alkenyl, $C_3$-$C_6$ haloalkenyl, $C_3$-$C_6$ alkynyl, $C_3$-$C_6$ haloalkynyl, $C_1$-$C_6$ alkoxy or $C_3$-$C_6$-cycloalkyl-$C_1$-$C_6$-alkyl;
$R^5$ is H, $NH_2$, $C_1$-$C_6$ alkyl or $C_3$-$C_6$ alkynyl;
$R^6$ is H or $C_1$-$C_6$ alkyl;
W is O or S; and
Z is O or S;
by
ii) reacting the 4-substituted amino-benzoxazinone of formula (I) with 1,1'-carbonyldiimidazole (CDI) and a (thio)urea compound of formula (V),

wherein $R^5$, $R^6$ and Z are defined as in formula (IV);
to obtain the triazinon-benzoxazinone of formula (IV).

In a preferred embodiment step ii) is carried out in the presence of a base.

The NH-benzoxazinones of formula (II) can be prepared by reacting dinitro compounds of formula (VI-1) with a reducing agent to give diamino compounds of formula (VII) and subsequently treating the diamino compounds of formula (VII) with an acid:

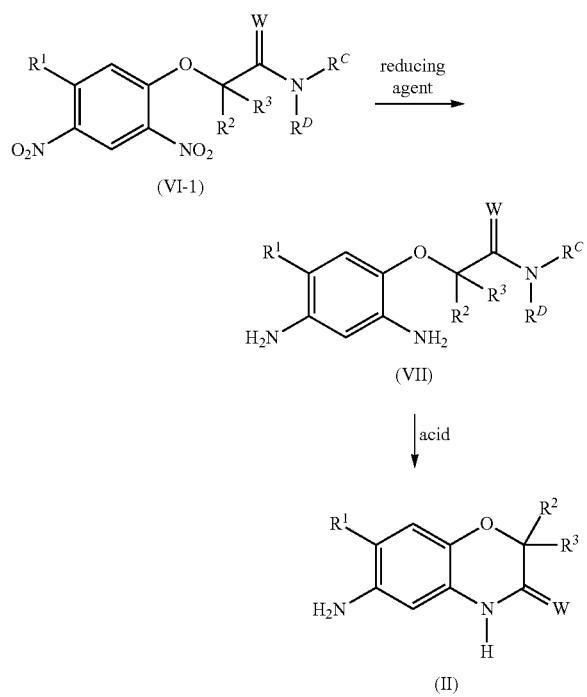

wherein
$R^C$, $R^D$ are independently of each other $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl, wherein the phenyl and the benzyl ring are independently of one another unsubstituted or substituted by 1 to 5 substituents selected from the group consisting of halogen, $NO_2$, $C_1$-$C_6$-alkyl or $C_1$-$C_6$-alkoxy, or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents; and $R^1$, $R^2$, $R^3$ and W are defined as in formula (II) above.

Accordingly, in a further preferred embodiment of the process of the invention the 4-substituted amino-benzoxazinones of formula (I) are prepared by
a) reacting a dinitro compound of formula (VI-1) with a reducing agent to obtain a diamino compound of formula (VII);
b) treating the diamino compound of formula (VII) with an acid to obtain a NH-benzoxazinone of formula (II); and
c) reacting the NH-benzoxazinone of formula (II) with a base and a compound of formula (III).

The dinitro compounds of formula (VI-1) can be obtained by reacting haloacetamides of formula (VIII) with phenols of formula (IX) in the presence of a base to give aryloxyacetamides of formula (VI) and, if $R^A$ and/or $R^B$ in formula (VI) are H, subsequently treating the aryloxyacetamides of formula (VI) with $HNO_3$/$H_2SO_4$:

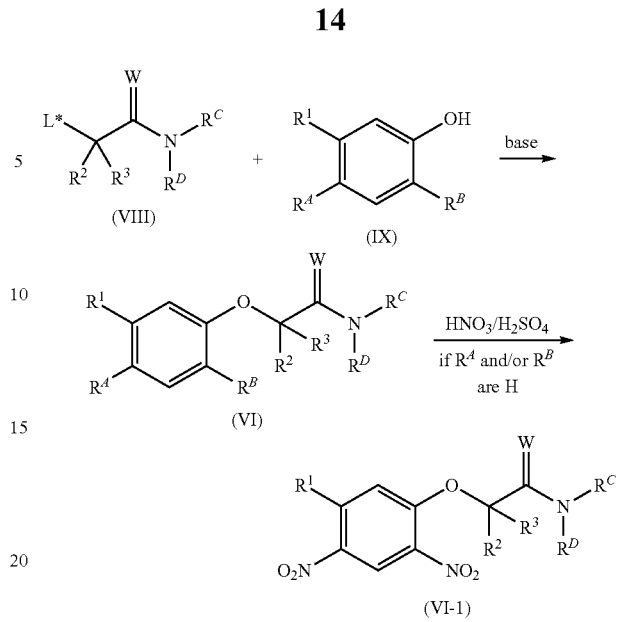

wherein
$R^A$, $R^B$ are independently H or $NO_2$;
L* is halogen;
$R^1$, $R^2$, $R^3$ and W are defined as in formula (II) above; and
$R^C$ and $R^D$ are defined as above.

The phenol of formula (IX) that is converted into the aryloxyacetamide of formula (VI) can also be used in the form of a salt, for example in form of its alkali metal or alkaline metal salt, preferably in the form of its sodium, potassium, magnesium or calcium salt. If a salt of the phenol of formula (IX) is used, the addition of a base is not necessary.

Accordingly, in a further preferred embodiment of the process of the invention the 4-substituted amino-benzoxazinone of formula (I) are prepared by
a) reacting an haloacetamide of formula (VIII) with a phenol of formula (IX) in the presence of a base to obtain an aryloxyacetamide of formula (VI);
b) if $R^A$ and/or $R^B$ in formula (VI) are H:
reacting the aryloxyacetamide of formula (VI) with $HNO_3$/$H_2SO_4$ to obtain a dinitro compound of formula (VI-1);
c) reacting the dinitro compound of formula (VI-1) with a reducing agent to obtain a diamino compound of formula (VII);
d) treating the diamino compound of formula (VII) with an acid to obtain a NH-benzoxazinone of formula (II); and
e) reacting the NH-benzoxazinone of formula (II) with a base and a compound of formula (III) to obtain a 4-substituted amino-benzoxazinone of formula (I).

With respect to the variables within the compounds of formulae (IV), (V), (VI), (VI-1), (VII), (VIII) or (IX), the particularly preferred embodiments of the compounds of formulae (IV), (V), (VI), (VI-1), (VII), (VIII) or (IX) correspond, either independently of one another or in combination with one another, to those of the variables of $R^1$, $R^2$, $R^3$, $R^4$, W and L of formulae (I), (II) or (III), or have, either independently of one another or in combination with one another, the following meanings:

$R^C$ and $R^D$ preferably are independently of each other $C_1$-$C_6$-alkyl, $C_1$-$C_6$-cyanoalkyl, $C_1$-$C_6$-hydroxyalkyl, $C_1$-$C_6$-alkoxy-$C_1$-$C_6$-alkyl, $C_3$-$C_6$-cycloalkyl, phenyl or benzyl, wherein the phenyl and the benzyl ring are independently of one another unsubstituted or substituted by 1 to 3 substituents selected from the group consisting of halogen, $C_1$-$C_6$-alkyl or $C_1$-$C_6$-alkoxy, or $R^C$ and $R^D$ together with the N atom which they are attached to, represent a saturated or aromatic 5- to 6-membered ring, optionally containing 1 additional heteroatom from the group O and N, with the ring optionally being substituted with 1 to 2 $C_1$-$C_6$-alkyl substituents;

particularly preferred are independently of each other $C_1$-$C_4$-alkyl, $C_1$-$C_4$-hydroxyalkyl, $C_1$-$C_6$-alkoxy-$C_1$-$C_4$-alkyl or benzyl, wherein the benzyl ring is unsubstituted or substituted by 1 to 3 substituents selected from the group consisting of halogen, $C_1$-$C_4$-alkyl or $C_1$-$C_4$-alkoxy, especially preferred the benzyl ring is unsubstituted, or $R^C$ and $R^D$ together with the N atom which they are attached to, represent a saturated 5- to 6-membered ring, optionally containing 1 additional oxygen atom, with the ring optionally being substituted with 1 to 2 $C_1$-$C_6$-alkyl substituents;

L* is preferably Cl, Br or I, particularly preferred Cl or Br, especially preferred Br;

$R^5$ is preferably $NH_2$, $C_1$-$C_6$-alkyl or $C_3$-$C_6$-alkynyl; also preferably H or $C_1$-$C_6$-alkyl; more preferably $C_1$-$C_6$-alkyl; most preferably $C_1$-$C_4$-alkyl; particularly preferred $CH_3$;

$R^6$ is preferably $C_1$-$C_6$-alkyl; more preferably $C_1$-$C_4$-alkyl; most preferably $CH_3$;

Z is preferably O, is also preferably S.

In a further aspect of the invention there is provided the compound of formula (I.a.35)

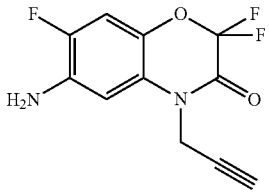

(I.a.35)

The invention is illustrated by the following examples without being limited thereto or thereby.

1. Preparation of 4-Substituted Amino-Benzoxazinones of Formula (I)

EXAMPLES 1.1 TO 1.5

6-Amino-2,2,7-trifluoro-4-prop-2-ynyl-4H-benzo[1,4]oxazin-3-one

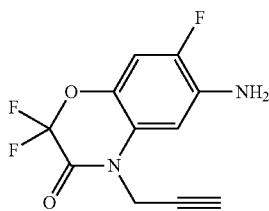 [SMILES: C#CCN1C(=O)C(F)(F)Oc2cc(F)c(N)cc21]

EXAMPLE 1.1

61.0 g (0.2678 mol) 6-amino-2,2,7-trifluoro-4H-benzo[1,4]oxazin-3-one, 360 g ethyl acetate and 38.9 g (0.2815 mol) potassium carbonate were initially charged at 25° C. in a stirred vessel. 43.8 g (0.2945 mol) propargyl bromide (80% w/w in toluene) were added at 25-30° C. within 15 minutes. Thereafter the reaction mixture was stirred at 78° C. for 8 hours and then cooled to 25° C. The precipitated salt was filtered off and washed with 360 g of ethyl acetate. The combined ethyl acetate solutions were washed with 200 g hydrochloric acid (1%) and twice with 200 g water. The organic phase was dried by azeotropic distillation (ca. 600 g distillate). The remaining solution (158.5 g) comprised 40.3% by weight of the desired product (HPLC analysis with external standard). The yield (based on the amino compound used) was 93.1%.

From a small quantity of the solution the solvent was completely distilled off at reduced pressure. The remaining residue was recrystallized from methanol and dried. The obtained crystals (melting point: 239.2° C.) showed the following spectroscopical data:

1H-NMR (500 MHz, DMSO-d6): δ (ppm)=3.45 (s, 1H), 4.74 (s, 2H), 5.42 (s, 2H), 6.85 (d, 1H), 7.26 (d, 1H)

EXAMPLE 1.2

219.1 g (1.0 mol) 6-amino-2,2,7-trifluoro-4H-benzo[1,4]oxazin-3-one, 1100 g dimethylformamide and 145.5 g (1,053 mol) potassium carbonate were initially charged at 25° C. in a stirred vessel. 163.2 g (1.1 mol) propargyl bromide (80% w/w in toluene) were added at 25-30° C. within 30 minutes. Thereafter the reaction mixture was stirred at 60° C. for 2 hours and then cooled to 25° C. The precipitated salt was filtered off and washed with 3300 g of ethyl acetate. The combined organic solutions were washed with 750 g water and with 750 g sodium sulfate solution (5%). The combined inorganic phases were extracted three times with 550 g ethyl acetate. All organic phases were combined and dried by azeotropic distillation. The remaining solution (635.3 g) comprised 40.05% by weight of the desired product (HPLC analysis with external standard). The yield (based on the amino compound used) was 97.8%.

EXAMPLE 1.3

0.8 g (0.00348 mol) 6-amino-2,2,7-trifluoro-4H-benzo[1,4]oxazin-3-one (purity: 94.9%) were dissolved in 19.76 g ethyl acetate at 20° C. 0,075 g ethyltrimethylammoniumiodide and 0.284 g (0.00205 mol) potassium carbonate were added. Then 0.463 g (0.00435 mol) propargyl chloride (70% in toluene) were added. The mixture was heated to reflux (73-77° C.) over 10 h. Reaction mixture was cooled to 25° C. and 20 g water was added under stirring. Phases were separated. The organic phase was evaporated to dryness at 45° C./4 mbar. 0.9 g solid with a purity of 95.0% (determined by quantitative HPLC) were isolated (yield: 95.9%).

EXAMPLE 1.4

0.8 g (0.00348 mol) 6-amino-2,2,7-trifluoro-4H-benzo[1,4]oxazin-3-one (purity: 94.9%) were dissolved in 20 g ethyl acetate at 20° C. 0.505 g (0.00365 mol) potassium carbonate and 0.614 g (0.00435 mol) propargyl mesylate (95%) were added as solid. The mixture was heated to reflux (77° C.) over 3 h. Reaction mixture was cooled to 25° C. and 20 g water was added under stirring. Phases were separated. The organic phase was evaporated to dryness at 45° C./4 mbar. 1.0 g solid with a purity of 88.1% (determined by quantitative HPLC) were isolated (yield: 98.9%).

EXAMPLE 1.5

13.22 g (0.06 mol) 6-amino-2,2,7-trifluoro-4H-benzo[1,4]oxazin-3-one (purity: 99%) were dissolved in 48 g DMF at 20° C. 10.67 g (0.077 mol) potassium carbonate and 7.98 g (0.075 mol) propargyl chloride (70% in toluene) were added. The mixture was stirred at 72° C. for 2 h. Reaction mixture was cooled to 3° C. and 120 g water were added under stirring over a period of 2 h at 3-5° C. Suspension was stirred for 3 h at 0-5° C. The solid was filtered off and washed with water. The wet solid was dried in a vacuum cabinet at 50° C./3 mbar over 17 hours. 14.8 g of a light brown solid with a purity of 99.3% (determined by quant. HPLC) were isolated (yield: 95.6%).

2. Preparation of NH-Benzoxazinones of Formula (II)

EXAMPLE 2.1

6-amino-2,2,7-trifluoro-4H-benzo-[1,4]oxazin-3-one from 2,2-difluoro-2(2,4-dinitro-5-fluoro-phenoxy)]-N,N-dimethyl-acetamide

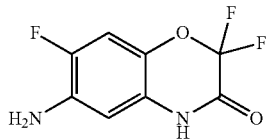 [SMILES: Nc1cc2c(cc1F)OC(F)(F)C(=O)N2]

To a solution of 2,2-difluoro-2-(2,4-dinitro-5-fluoro-phenoxy)-N,N-dimethyl-acetamide (60.0 g, 186 mmol) in toluene (432 g) was added Pd on charcoal (5% Pd, 50% water content, 1.1 mmol). Thereafter MeOH (492 g) was added and the mixture was stirred under an atmosphere of hydrogen (over pressure 0.1 bar) at 45° C. for 2 h. After completion of the reaction the pressure was released, concentrated HCl (36.5%, 22 g, 220 mmol) added and the reaction mixture heated to reflux for further 1 h. The catalyst was filtered off, the pH adjusted with NaOH to 9 and the MeOH distilled off under reduced pressure. After addition of water (200 g) and stirring for 1 h the precipitate was filtered off, washed twice with water (100 g) and dried at 50° C. under reduced pressure. The product was obtained as a tan solid (38.9 g, 90% pure by NMR, 160 mmol, 86% yield).

$^1$H NMR (DMSO-$d_6$, 500 MHz): δ (ppm)=11.9 (bs, 1 H); 7.15 (d, J=11.0 Hz, 1 H); 6.55 (d, J=8.5 Hz, 1 H); 5.28 (bs, 2 H).

$^{13}$C NMR (DMSO-$d_6$, 125 MHz): δ (ppm)=153.7 (t, J=38 Hz); 146.1 (d, J=235 Hz); 133.9 (d, J=15 Hz); 127.3 (d, J=11 Hz); 120.9 (d, J=3 Hz); 113.1 (t, J=260 Hz); 104.9 (d, J=24 Hz); 102.4 (d, J=5 Hz).

3. Preparation of Diamino Compounds of Formula (VII)

EXAMPLE 3.1

Synthesis of 2,2-difluoro-2-(2,4-diamino-5-fluoro-phenoxy)-N,N-dimethyl-acetamide

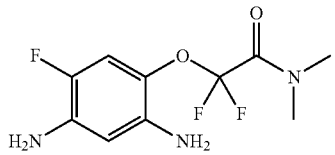

To a solution of 2,2-difluoro-2-(2,4-dinitro-5-fluoro-phenoxy)-N,N-dimethyl-acetamide (22.0 g, 68.1 mmol) in toluene (200 g) obtained according to example 4.1 alternative 2 Pd/C (10% Pd, dry catalyst, 0.7 g, 0.7 mmol) was added. Thereafter, MeOH (80 g) was added and the mixture was stirred under an atmosphere of hydrogen (pressure of 0.1 bar) at 45° C. for 90 min. After completion of the reaction the pressure was released, the catalyst was filtered off and the filtrate was evaporated to dryness. The product (17.3 g, 84% pure by NMR, 55.2 mmol, 81% yield) was obtained as an off-white solid. If desired, the purity can be increased by chromatography (SiO$_2$, cyclohexane/EtOAc mixtures).

$^1$H NMR (DMSO-$d_6$, 500 MHz): δ (ppm)=6.79 (d, J=11.0 Hz, 1 H); 6.16 (d, J=8.5 Hz, 1 H); 4.95 (bs, 2 H); 4.60 (bs, 2 H); 3.19 (s, 3 H); 2.96 (bs, 3 H).

$^{13}$C NMR (DMSO-$d_6$, 125 MHz): δ (ppm)=158.3 (t, J=35 Hz); 141.7 (d, J=278 Hz); 137.6; 134.9 (d, J=14 Hz); 123.9 (d, J=9 Hz); 115.8 (t, J=272 Hz); 109.2 (d, J=22 Hz); 102.0 (d, J=4 Hz); 36.9; 36.2.

EXAMPLE 3.2

Synthesis of 2,2-difluoro-2-(2,4-diamino-5-fluoro-phenoxy)-N,N-diethyl-acetamide

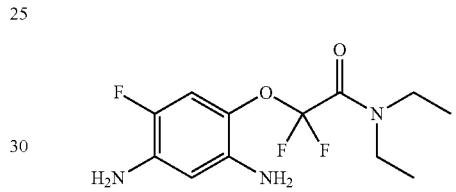

A solution of 2,2-difluoro-2-(2,4-dinitro-5-fluoro-phenoxy)-N,N-diethyl-acetamide (13.5 g, 38.4 mmol) obtained according to example 4.1 alternative 2, and Pd/C (10% Pd, dry catalyst, 2.0 g, 1.9 mmol) in MeOH (395) was stirred under an atmosphere of hydrogen (pressure of 0.1 bar) at 50° C. for 2 h. After completion of the reaction the pressure was released, the catalyst was filtered off and the filtrate was evaporated to dryness. The product was purified by column chromatography (SiO$_2$, cyclohexane/EtOAc mixtures). The product was obtained as an off-white solid (11.0 g, 88% pure by NMR, 33.2 mmol, 86% yield).

$^1$H NMR (CDCl$_3$, 500 MHz): δ (ppm)=6.85 (d, J=11.0 Hz, 1 H); 6.19 (d, J=8.5 Hz, 1 H); 3.71 (bs, 4 H); 3.58 (q, J=7.0 Hz, 2 H); 3.45 (q, J=7.0 Hz, 2 H); 1.25 (t, J=7.0 Hz, 3 H); 1.19 (t, J=7.0 Hz, 3 H).

$^{13}$C NMR (CDCl$_3$, 125 MHz): δ (ppm)=158.8 (t, J=35 Hz); 143.7 (d, J=231 Hz); 136.5; 133.5 (d, J=14 Hz); 126.9 (d, J=9 Hz); 116.1 (t, J=273 Hz); 110.3 (d, J=23 Hz); 103.8 (d, J=3 Hz); 42.4; 41.6; 14.1; 12.6.

4. Preparation of Dinitro Compounds of Formula (VI-1)

EXAMPLE 4.1

Synthesis of 2,2-difluoro-2-(2,4-dinitro-5-fluoro-phenoxy)-N,N-dimethyl-acetamide

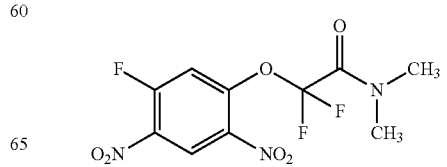

Alternative 1:

To a mixture of $H_2SO_4$ (98%, 34.5 g, 345 mmol) and $HNO_3$ (100%, 11.0 g, 175 mmol) at room temperature was added 2,2-difluoro-2-(3-fluoro-phenoxy)-N,N-dimethyl-acetamide (8.7 g, 37 mmol). The temperature rose to 40° C. and was kept at that temperature for further 3 h. The mixture was then poured on 100 g of ice-water. The precipitate was taken up in 50 g of toluene and the aqueous phase was extracted with 25 g of toluene. The combined org. phases were washed with saturated $NaHCO_3$ solution and water. The crude product (11.5 g, 82% purity by quant. HPLC, 29 mmol, 78% yield) was obtained after removal of all volatiles as a yellowish solid. Analytically pure material the crude material could be obtained after recrystallisation from cyclohexane/EtOAc (80:20).

Alternative 2:

A solution of 61.5 g $HNO_3$ (100%, 0.976 mol) and 433.7 g $H_2SO_4$ (96%, 4.245 mol) was prepared at 0-20° C. by addition of $HNO_3$ to the sulfuric acid (quantity of mixed acid: 495.2 g). 100 g 2,2-difluoro-2-(3-fluoro-phenoxy)-N,N-dimethyl-acetamide (99%, 0.425 mol) was filled into the reaction vessel at 0° C. 236.9 g of the mixed acid (portion 1) was added at a rate to keep the temperature between 0 and 10° C.

258.3 of the mixed acid (portion 2) was dosed at 40° C. Upon complete addition the mixture was kept at 40° C. for another 9 h. Then, it was cooled to 25° C. and poured to a mixture of 1000 g ice water and 500 ml toluene. Reactor was rinsed with 100 g water and 50 g toluene. The phases were separated at 20° C. The aqueous layer was extracted with 240 g toluene and then discarded. The combined organic layers were washed 4 times with 400 g water in each case (final pH-value of the organic phase: 3). The water in the remaining organic phase was removed by distilling off toluene/water at reduced pressure. The product was obtained as a solution in toluene: 541.3 g (concentration of the dinitro compound by quant. HPLC: 22.3%; yield: 88.1%).

$^1$H NMR ($CDCl_3$, 400 MHz): δ (ppm)=8.82 (d, J=7.5 Hz, 1 H); 7.52 (d, J=11.0 Hz, 1 H); 3.26 (s, 3 H); 3.11 (s, 3 H).

$^{13}$C NMR ($CDCl_3$, 100 MHz): δ (ppm)=157.1 (d, J=276 Hz); 156.7 (d, J=34 Hz); 147.6 (td, J=3 Hz, J=11 Hz); 136.9; 132.9 (d, J=9 Hz); 124.2; 115.3 (t, J=281 Hz); 111.7 (td, J=3 Hz, J=26 Hz); 36.8; 36.7.

Melting point: 66° C.

EXAMPLE 4.2

Synthesis of 2,2-difluoro-2-(2,4-dinitro-5-fluoro-phenoxy)-N,N-diethyl-acetamide

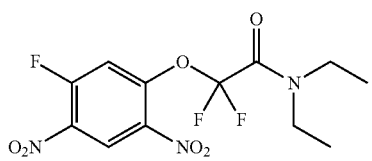 [SMILES: CCN(CC)C(=O)C(F)(F)Oc1cc(F)c(N)cc1N]

To a mixture of $H_2SO_4$ (98%, 261 g, 2.61 mol) and $HNO_3$ (100%, 107 g, 1.7 mol) at 0° C. was added 2,2-difluoro-2-(3-fluoro-phenoxy)-N,N-diethyl-acetamide (34 g, 130 mmol) with cooling. The mixture was then warmed to r.t. and stirred for further 3 h. Then, the mixture was poured on 750 g ice-water. TBME (250 mL) was added and the aqueous phase was extracted with TBME (200 mL). The combined organic phases were washed with water (300 mL), saturated $NaHCO_3$ solution and brine. Drying over $Na_2SO_4$ and evaporation of all volatiles gave the product as a yellow solid.

1H NMR ($CDCl_3$, 500 MHz): δ (ppm)=8.82 (d, J=7.5 Hz); 7.53 (q, J=11.0 Hz, 1 H); 3.57 (q, J=7.0 Hz, 2 H); 3.45 (q, J=7.0 Hz, 2 H); 1.27 (t, J=7.0 Hz, 3 H); 1.18 (t, J=7.0 Hz, 3 H).

$^{13}$C NMR ($CDCl_3$, 125 MHz): δ (ppm)=157.6 (d, J=268 Hz); 156.6 (t, J=34 Hz); 148.2 (d, J=11 Hz); 137.3; 133.3 (d, J=8 Hz); 124.7; 115.8 (t, J=281 Hz); 112.3 (d, J=26 Hz); 42.3; 42.0; 14.1; 12.2.

EXAMPLE 4.3

Synthesis of 2,2-difluoro-2-(2,4-dinitro-5-fluoro-phenoxy)-1-pyrrolidine-1-yl-ethanone

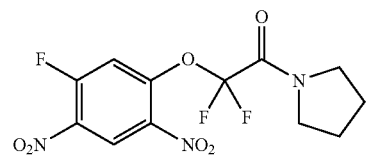 [SMILES: O=C(N1CCCC1)C(F)(F)Oc1cc(F)c([N+](=O)[O-])cc1[N+](=O)[O-]]

To a mixture of $H_2SO_4$ (98%, 22.0 g, 220 mmol) and $HNO_3$ (100%, 8.5 g, 135 mmol) at 0° C. was added 2,2-difluoro-2-(3-fluoro-phenoxy)-1-pyrrolidine-1-yl-ethanone (3.3 g, 12.7 mmol). The temperature rose to 10° C. and was kept at that temperature for further 16 h. The mixture was then poured on 150 g of ice-water and 80 mL of TBME. The aqueous phase was extracted with 50 mL of TBME. The combined org. phases were washed with saturated $NaHCO_3$ solution and water. The crude product (3.6 g, >98% purity by HPLC, 10.3 mmol, 81% yield) was obtained after removal of all volatiles as a yellow solid.

$^1$H NMR ($CDCl_3$, 500 MHz): δ (ppm)=8.81 (d, J=7.5 Hz, 1 H); 7.54 (d, J=11.0 Hz, 1 H); 3.72-3.78 (m, 4 H); 3.54-3.59 (m, 4 H); 2.02-2.09 (m, 4 H); 1.92-1.98 (m, 4 H).

$^{13}$C NMR ($CDCl_3$, 125 MHz): δ (ppm)=157.6 (d, J=274 Hz); 155.7 (t, J=34 Hz); 148.2 (d, J=11 Hz); 137.4; 133.3 (d, J=8 Hz); 124.7; 115.6 (t, J=280 Hz); 112.5 (d, J=32 Hz); 47.9; 47.0; 26.4; 23.5.

Melting point: 78° C.

EXAMPLE 4.4

Synthesis of 2,2-difluoro-2-(2,4-dinitro-5-fluoro-phenoxy)-1-morpholine-1-yl-ethanone

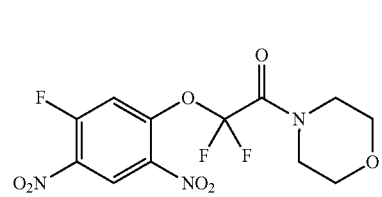 [SMILES: O=C(N1CCOCC1)C(F)(F)Oc1cc(F)c([N+](=O)[O-])cc1[N+](=O)[O-]]

To a mixture of $H_2SO_4$ (96%, 68.8 g, 701 mmol) and $HNO_3$ (100%, 13.3 g, 210 mmol) at 0° C. was added 2,2-difluoro-2-(3-fluoro-phenoxy)-1-morpholine-1-yl-ethanone (18.3 g, 90% pure, 60 mmol). The temperature was eventually increased to 40° C. and was kept at room temperature for 60 min. The mixture was then poured on 160 g of ice-water and 80 g of chlorobenzene. The aqueous phase was extracted with chlorobenzene (2×40 mL). The combined org. phases were washed with saturated $NaHCO_3$ solution and water. The crude product (12.3 g, >90% purity by HPLC) was obtained after removal of all volatiles as a reddish solid. Recrystallisation from n-BuOH (150 mL) gave the product as a yellow solid.

$^1$H NMR (CDCl$_3$, 500 MHz): δ (ppm)=8.82 (d, J=7.0 Hz, 1 H); 7.52 (d, J=10.5 Hz, 1 H); 3.68-3.78 (m, 8 H).

$^{13}$C NMR (CDCl$_3$, 125 MHz): δ (ppm)=157.5 (d, J=274 Hz); 155.8 (t, J=34 Hz); 147.6 (d, J=11 Hz); 137.2; 135.3; 124.7; 115.4 (t, J=281 Hz); 112.1 (d, J=26 Hz); 66.5; 66.4; 46.6; 43.8.

Melting point: 96° C.

5. Preparation of Aryloxyacetamides of Formula (VI)

EXAMPLE 5.1

Synthesis of 2,2-difluoro-2-(5-fluoro-2-nitro-phenoxy)-N,N-dimethyl-acetamide

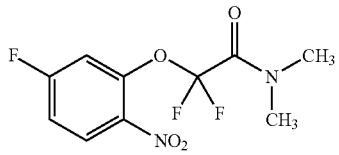

A mixture of 2-nitro-5-fluoro-phenol (3.0 g, 19.1 mmol), 2-bromo-2,2-difluoro-N,N-dimethylacetamide (3.9 g, 19.1 mmol) and Na$_2$CO$_3$ (2.1 g, 19.8 mmol) in 30 mL of DMAC was heated to 100° C. overnight. The mixture was then poured on 50 mL of H$_2$O and extracted with TBME (2×50 mL). The combined organic layers were washed with 10% NaOH (50 mL) and dried over Na$_2$SO$_4$. The crude product was obtained after evaporation of all volatiles. Purification by chromatography on silica gave the product (1.8 g, 6.4 mmol, 38% yield) as a yellow oil that solidified upon standing.

$^1$H NMR (CDCl$_3$, 500 MHz): δ (ppm)=8.04 (dd, J=5.5 Hz, J=9.0 Hz, 1 H); 7.26-7.29 (m, 1 H); 7.13 (dd, J=2.5 Hz, J=7.5 Hz, 1 H); 3.25 (s, 3 H); 3.09 (s, 3 H).

$^{13}$C NMR (CDCl$_3$, 125 MHz): δ (ppm)=164.5 (d, J=258 Hz); 157.9 (t, J=34 Hz); 143.9 (d, J=11 Hz); 138.9; 127.9 (d, J=11 Hz); 115.5 (t, J=278 Hz); 113.6 (d, J=10 Hz); 110.9 (d, J=28 Hz); 37.2; 37.1.

The invention claimed is:

1. A process for manufacturing 4-substituted amino-benzoxazinones of formula (I),

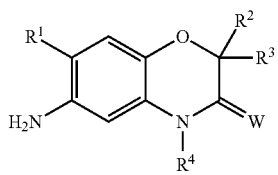

wherein
R$^1$ is H or halogen;
R$^2$ is halogen;
R$^3$ is H or halogen;
R$^4$ is C$_1$-C$_6$-alkyl, C$_1$-C$_6$-haloalkyl, C$_3$-C$_6$-cycloalkyl, C$_3$-C$_6$-alkenyl, C$_3$-C$_6$-haloalkenyl, C$_3$-C$_6$-alkynyl, C$_3$-C$_6$-haloalkynyl, C$_1$-C$_6$-alkoxy or C$_3$-C$_6$-cycloalkyl-C$_1$-C$_6$-alkyl; and
W is O or S;

wherein
a NH-benzoxazinone of formula (II),

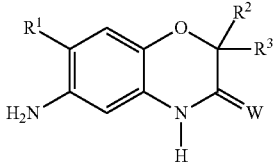

or a salt thereof,
wherein R$^1$, R$^2$, R$^3$ and W are defined as in formula (I); is reacted with a compound of formula (III),

R$^4$-L (III)

wherein R$^4$ is defined as in formula (I);
L is halogen or OS(O)$_2$R$^7$; and
R$^7$ is C$_1$-C$_6$-alkyl, C$_1$-C$_6$-haloalkyl, C$_1$-C$_6$-nitroalkyl, C$_1$-C$_6$-alkoxy-C$_1$-C$_6$-alkyl, C$_3$-C$_6$-cycloalkyl, phenyl or phenyl-C$_1$-C$_6$-alkyl, wherein each phenyl ring independently of one another is unsubstituted or substituted by 1 to 5 substituents selected from the group consisting of halogen, CN, NO$_2$, C$_1$-C$_6$-alkyl, C$_1$-C$_6$-haloalkyl or C$_1$-C$_6$-alkoxy;
in the presence of a base.

2. The process according to claim 1, wherein the base is selected from the group consisting of carbonates, hydrogen carbonates, hydroxides, oxides, phosphates and alkoxides.

3. The process according to claim 1, wherein the base is selected from carbonates.

4. The process according to claim 1, wherein R$^1$ and R$^3$ are halogen.

5. The process according to claim 1, wherein
R$^2$ is F; and
W is O.

6. The process according to claim 1, wherein R$^4$ is C$_3$-C$_6$-alkynyl.

7. The process according to claim 1, wherein a NH-benzoxazinone of formula (II) is employed.

8. The process according to claim 1, wherein the NH-benzoxazinone of formula (II) is prepared by
a) reacting a dinitro compound of formula (VI-1)

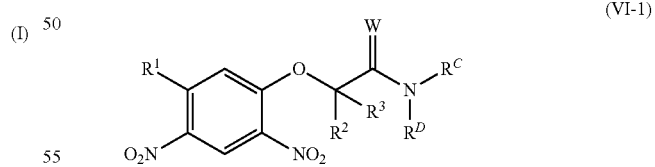

wherein R$^1$, R$^2$, R$^3$ and W are defined as in claim 1; and
R$^C$, R$^D$ are independently of each other C$_1$-C$_6$-alkyl, C$_2$-C$_6$-alkenyl, C$_2$-C$_6$-alkynyl, C$_1$-C$_6$-haloalkyl, C$_1$-C$_6$-cyanoalkyl, C$_1$-C$_6$-nitroalkyl, C$_1$-C$_6$-hydroxyalkyl, C$_1$-C$_6$-alkoxy-C$_1$-C$_6$-alkyl, amino-C$_1$-C$_6$-alkyl, (C$_1$-C$_6$-alkyl)amino-C$_1$-C$_6$-alkyl, di(C$_1$-C$_6$-alkyl)amino-C$_1$-C$_6$-alkyl, C$_3$-C$_6$-cycloalkyl, phenyl or benzyl,
wherein the phenyl and the benzyl ring are independently of one another unsubstituted or substituted by 1 to 5 substituents selected from the group consisting of halogen, $NO_2$, $C_1$-$C_6$-alkyl or $C_1$-$C_6$-alkoxy, or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents with a reducing agent to obtain a diamino compound of formula (VII)

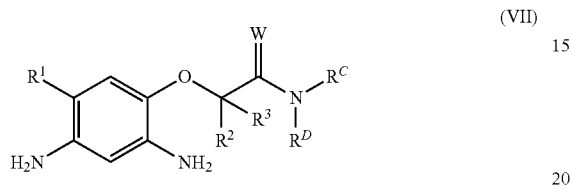

(VII)

wherein $R^1$, $R^2$, $R^3$ and W are defined as in claim 1, and $R^C$ and $R^D$ are defined as above;

treating the diamino compound of formula (VII) with an acid to obtain an NH-benzoxazinone of formula (II).

\* \* \* \* \*